US012623039B2

(12) United States Patent
Tupper et al.

(10) Patent No.: US 12,623,039 B2
(45) Date of Patent: May 12, 2026

(54) MEDICO-SURGICAL APPARATUS

(71) Applicant: SMITHS MEDICAL INTERNATIONAL LIMITED, Ashford (GB)

(72) Inventors: Steven Mark Tupper, Hythe (GB); Jamie Daniel Perkins, Ashford (GB); Steven James Field, Bridge Canterbury (GB)

(73) Assignee: ICU MEDICAL INTERNATIONAL LIMITED, Ashford (GB)

( * ) Notice: Subject to any disclaimer, the term of this patent is extended or adjusted under 35 U.S.C. 154(b) by 776 days.

(21) Appl. No.: 17/926,169

(22) PCT Filed: May 28, 2021

(86) PCT No.: PCT/GB2021/000063
§ 371 (c)(1),
(2) Date: Nov. 18, 2022

(87) PCT Pub. No.: WO2021/245368
PCT Pub. Date: Dec. 9, 2021

(65) Prior Publication Data
US 2023/0191060 A1 Jun. 22, 2023

(30) Foreign Application Priority Data
Jun. 3, 2020 (GB) ..................................... 2008340

(51) Int. Cl.
*A61M 16/04* (2006.01)
*A61M 16/10* (2006.01)
(52) U.S. Cl.
CPC .... *A61M 16/0468* (2013.01); *A61M 16/1045* (2013.01)

(58) Field of Classification Search
CPC .......... A61M 16/0465; A61M 16/0468; A61M 16/1045; A61M 16/201
See application file for complete search history.

(56) References Cited

U.S. PATENT DOCUMENTS 5,259,378 A * 11/1993 Huchon ............ A61M 16/0468
128/201.13
5,606,966 A 3/1997 Smith
(Continued)

FOREIGN PATENT DOCUMENTS

CN 206081256 U 4/2017
JP H067747 2/1994
(Continued)

OTHER PUBLICATIONS

PCT International Search Report for PCT/GB2021/000063 dated Aug. 27, 2021.
PCT Written Opinion for PCT/GB2021/000063 dated Aug. 27, 2021.

*Primary Examiner* — Joseph D. Boecker
(74) *Attorney, Agent, or Firm* — Louis Woo

(57) ABSTRACT

Apparatus (20) for fitting to the machine end of a tracheostomy tube (10) includes both an HME and a speaking valve (30). The HME includes two exchange elements (28, 29) at opposite ends of a housing (23) extending laterally of a coupling (25) for fitting on the tube. The speaking valve has a cylindrical sleeve (31) extending across the housing midway along its length and in line with the tube. The sleeve is rotatable about its axis and has two openings (36) on opposite sides that can be aligned with the exchange elements of the HME to allow gas to flow from the tube through the exchange elements, bypassing the speaking valve. When the patient wishes to speak, he twists and rotates the speaking valve to block flow to the exchange elements and instead to allow air to be inhaled via the valve.

8 Claims, 3 Drawing Sheets

(56)           References Cited

U.S. PATENT DOCUMENTS

| | | | |
|---|---|---|---|
| 6,668,831 B1 | 12/2003 | Hegwood | |
| 2002/0156527 A1 * | 10/2002 | Persson | A61F 2/20 |
| | | | 623/9 |
| 2007/0251523 A1 * | 11/2007 | Landuyt | A61M 16/047 |
| | | | 128/203.12 |
| 2014/0352691 A1 | 12/2014 | Shikani | |
| 2016/0206846 A1 | 7/2016 | Blom | |
| 2016/0242900 A1 | 8/2016 | Fahl | |
| 2016/0256649 A1 | 9/2016 | Hesselmar | |
| 2018/0015246 A1 * | 1/2018 | Kanazawa | A61M 16/206 |

FOREIGN PATENT DOCUMENTS

| | | | |
|---|---|---|---|
| JP | H08501948 A | 3/1996 | |
| JP | 3016861 B2 | 3/2000 | |
| JP | 2003501141 A | 1/2003 | |
| JP | 4156832 B2 | 9/2008 | |
| WO | 9701366 A1 | 1/1997 | |

* cited by examiner

MEDICO-SURGICAL APPARATUS

This invention relates to medico-surgical apparatus adapted for fitting with the machine end of a tracheostomy tube.

The invention is more particularly concerned with apparatus in the form of combined HME and speaking valve.

Where a patient breathes through a tube inserted in the trachea, such as a tracheostomy or endotracheal tube, gas flow to the bronchi is not warmed and moistened by passage through the nose. Unless the gas is warmed and moistened in some way it can cause damage and discomfort in the patient's throat. The gas can be conditioned by a humidifier in the ventilation circuit but, most conveniently, a heat and moisture exchange device (HME) is used. HMEs are small, lightweight devices including one or more HME exchange elements. When the patient exhales, gas passes through the exchange element and gives up a major part of its heat and moisture to the element. When the patient inhales, gas passes through the exchange element in the opposite direction and takes up a major part of the heat and moisture in the exchange element so that the gas inhaled by the patient is warmed and moistened. HME devices also help protect the patient from airborne contaminants like dust and bacteria. These HMEs are low cost and are disposable after a single use. They can be connected in a breathing circuit or simply connected to the machine end of a tracheal tube and left open to atmosphere where the patient is breathing spontaneously. HMEs can be used with other breathing devices such as face masks. HMEs are sold by Smiths Medical under the Thermovent® mark (Thermovent is a registered trade mark of Smiths Medical) and by other medical device companies.

Patients with a tracheostomy may be conscious and can be enabled to speak while the tube is inserted by means of a speaking valve connected to the external, machine end of the tracheostomy tube. Such speaking valves have a one-way mechanism that allows air to be inhaled through the valve by the patient but closes to prevent air being exhaled through the speaking valve. Instead, when the patient exhales, the air from the lungs by-passes the tube and flows up through the patient's vocal folds. Where the tracheostomy tube has a sealing cuff towards its patient end this is either deflated when speech is required or the wall of the tube is formed with fenestrations on the machine side of the seal so that air can flow out through the fenestrations above the cuff. Speaking valves are sold by Smiths Medical under the Orator® trade mark (Orator is a registered trade mark of Smiths Medical) and by other medical device companies.

Up to now it has only been possible for a patient to benefit from either a speaking valve or an HME but not to have both fitted at the same time. So, if a patient needs to speak, he must first disconnect the HME and then connect the speaking valve. Once the need for speech has passed the patient must remove the speaking valve and reconnect the HME. This repeated connection and disconnection to the tracheostomy tube can cause discomfort to the patient.

It is an object of the present invention to provide alternative medico-surgical apparatus.

According to one aspect of the present invention there is provided medico-surgical apparatus of the above-specified kind, characterised in that the apparatus includes a housing having both a one-way speaking valve and at least one HME element, and that the apparatus is arranged such that in one state flow through the HME element is enabled preferentially to flow through the speaking valve and in another state inhalation flow through the speaking valve is enabled preferentially to flow through the HME element.

The speaking valve preferably has a portion arranged to block a passage through the HME element in the other state. The portion of the speaking valve is preferably a cylindrical sleeve angularly displaceable within the housing, the sleeve having an opening that aligns with an HME element in the one state. The speaking valve may be fitted with the housing in a manner that enables the valve to be displaced out of the housing by an excessive expiratory force. The apparatus preferably has a coupling adapted for fitting with the machine end of the tracheostomy tube, a body portion extending transversely of the coupling, an HME element at opposite ends of the body portion and a cavity aligned with the coupling in which the speaking valve is angularly displaceably received for displacement between the one and other states. Alternatively, the apparatus may include occlusion means operable separately of the speaking valve to prevent or enable flow through the or each HME element. The occlusion means may be pneumatically operable, and the apparatus may include a pneumatic actuator. The occlusion means may include a bellows expansible to block flow through the or each HME element.

According to another aspect of the present invention there is provided an assembly of a tracheostomy tube and apparatus according to the above one aspect of the present invention, wherein the apparatus is fitted with the machine end of the tracheostomy tube.

An HME device and an assembly of an HME device fitted with a tracheostomy tube according to the present invention will now be described, by way of example, with reference to the accompanying drawings, in which.

Figure 1:
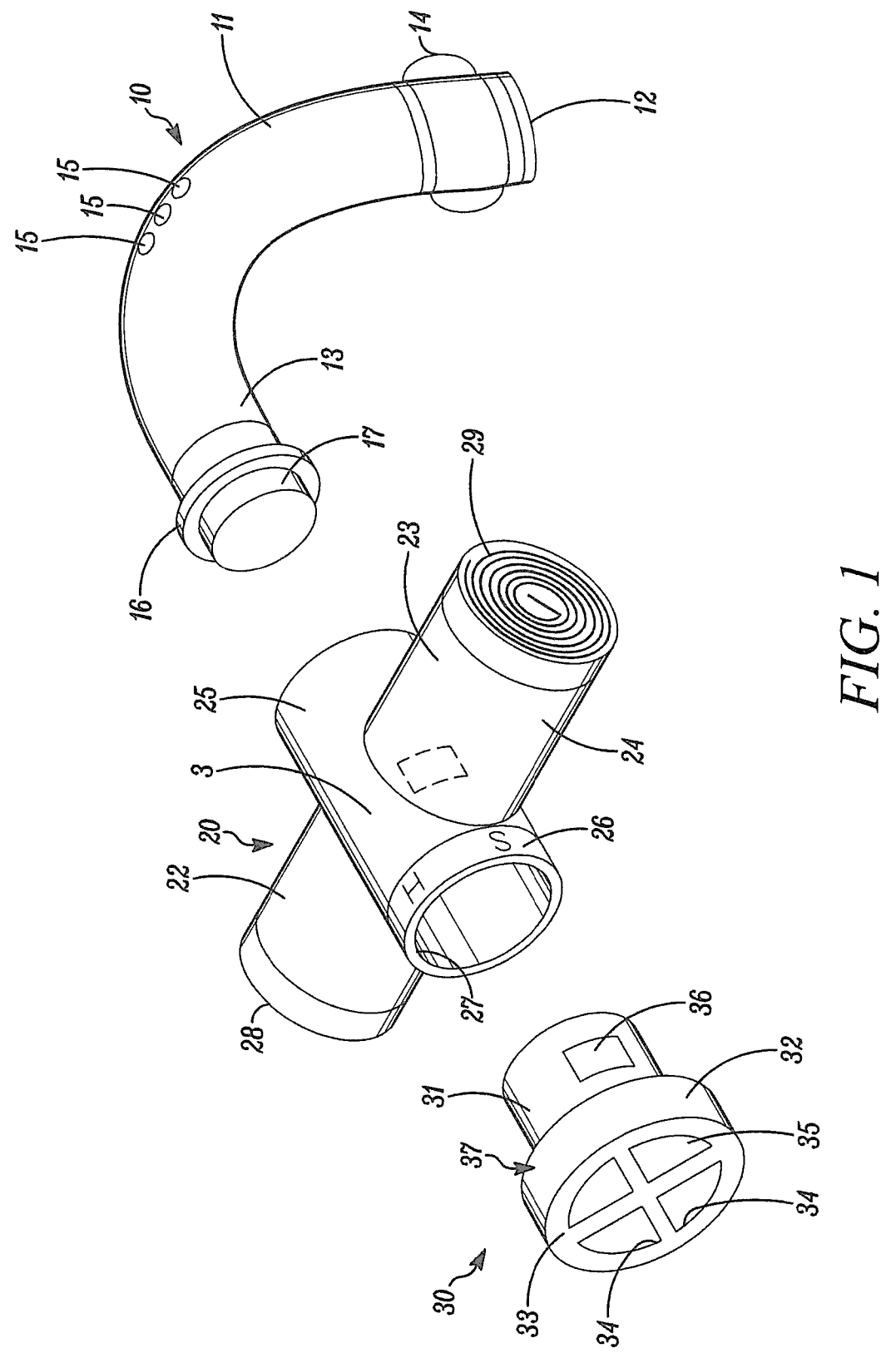
FIG. 1 is a perspective view of an assembly of a combined speaking valve and HME for a tracheostomy tube with the HME, speaking valve and tracheostomy tube shown separated before use.
Figure 2:
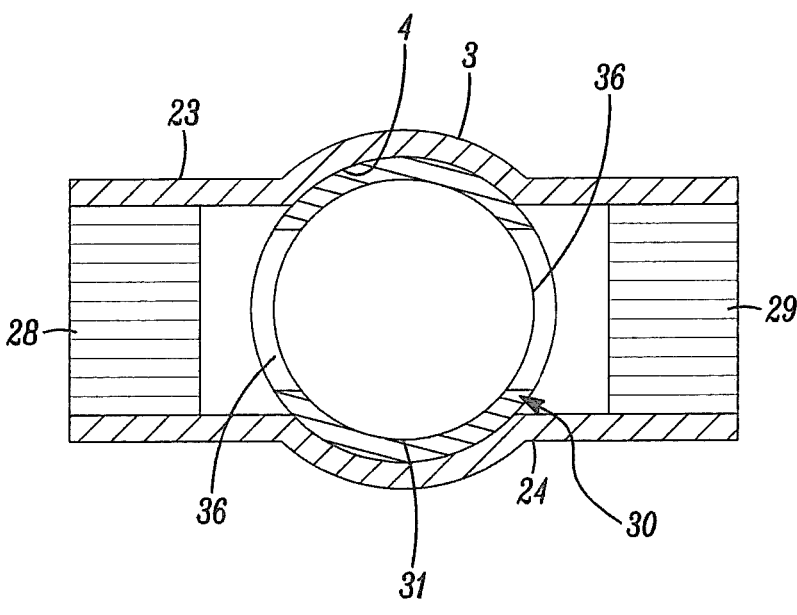
FIG. 2 is a sectional side elevation of the combined speaking valve and HME along the axis of the main body portion of the HME and with the speaking valve positioned to enable flow to and from the HME elements.
Figure 3:
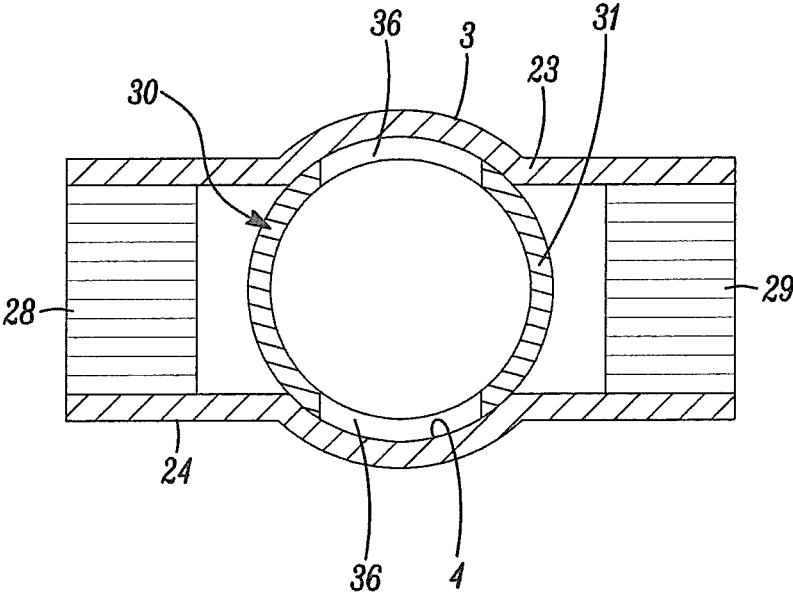
FIG. 3 shows the combined speaking valve and HME with the speaking valve displaced to block flow to the HME elements.

With reference first to FIGS. 1 to 3 there is shown an assembly of a tracheostomy tube 10 and medico-surgical apparatus 20 in the form of a combined speaking valve 30 and HME 22. For clarity the tracheostomy tube 10 is shown separate from the apparatus 20, with the speaking valve 30 being shown separate from the HME device 22, before assembly for use.

The tracheostomy tube 10 is of a conventional kind having a curved shaft 11 with a patient end 12 and a machine end 13. The tube 10 has an inflatable sealing cuff 14 close to its patient end 12. The shaft 11 is formed with several fenestrations or openings 15 spaced above the sealing cuff 14. The tube 10 also includes a conventional coupling 16 fitted in its machine end 13 and formed at its outer end with a male tapered 15 mm connector surface 17.

The HME device 22 has a generally T-shape configuration with an outer housing 23 having a main lateral body portion 24 of tubular shape and circular section. The housing 23 also has a coupling in the form of a short sleeve 25 of circular section projecting radially outwardly of the main body portion 24 on one side. Internally, the sleeve 25 is formed at its forward end with a female tapered surface adapted to mate with the connector surface 17 on the coupling 16. The HME device 22 also has a short circular collar 26 aligned with the sleeve 25 and projecting a short distance on the opposite side of the main body portion 24. The inner surface 27 of the collar 26 is adapted to receive the forward end portion 31 of the speaking valve 30. The outer surface of the sleeve 25 and the collar 26 form a continuation with a cylindrical surface 3 extending centrally across the main body portion 24. Internally, the cylindrical surface 3 defines a cylindrical cavity 4 (FIGS. 2 and 3). The HME device 22 is completed by two conventional HME elements 28 and 29 mounted in opposite ends of the main body portion 24. The HME elements 28 and 29 are of a conventional kind and could be formed by a coiled strip of corrugated paper treated with a hygroscopic salt to increase its ability to absorb water. Alternatively, the HME elements could be of a treated foam. Alternative HMEs could have just one HME element and could be of different configurations such as, for example, having a cross-section that was non-circular.

The speaking valve 30 is of generally cylindrical shape with a forward, patient end sleeve portion 31 adapted to be a close sealing fit within the inside wall 27 of the collar 26. The opposite, rear end of the speaking valve 30 has a short, enlarged head 32 of circular shape, the forward end of which abuts the outer end of the collar 26. The head 32 is closed by an end face 33 with several openings 34. The head 32 encloses a flexible flap valve 35 attached centrally to the centre of the inside of the end face 33. The flap valve 35 is arranged to allow air flow into the valve 30 through the openings 34 and to prevent flow in the opposite direction. The construction of the speaking valve 30 does not completely prevent all exhalation through the valve but prevents sufficient flow so that the majority is diverted for speech. The speaking valve 30, therefore, allows the patient to inhale through the valve but prevents exhalation through the valve. The speaking valve 30 is modified by the inclusion of two side openings 36 in the wall of the forward end portion 31 and arranged diametrically opposite one another. The length of the forward end portion 31 is such that it extends in the cavity 4 across the width of the lateral body portion 24. The speaking valve 30 may be a snap fit in the housing 23 by the provision of mating formations on the outside of the forward end portion 31 and on the inside of the housing 23. The engagement of the speaking valve 30 in the housing 23 is arranged to limit angular displacement of the speaking valve through 90° between a speech position, where the side openings 36 are blocked, and an HME position where the side openings open onto the HME elements 28 and 29. The head 32 of the speaking valve 30 has a marking 37 such as an arrow that can be positioned against one of two different markings "S" for speech and "H" around the collar 26 of the HME housing 23. The speaking valve 30 or the housing 23 may include cooperating detents at the extremes of angular displacement so that the speech valve clicks out of one extreme position and clicks into the other extreme position. In this way, manual force must be exerted to change the apparatus 20 from one mode or state to the other. The fitting of the speaking valve 30 within the housing 23 is preferably sufficiently strong to retain the speaking valve in the housing during normal use but to allow the speaking valve to pop out of the housing if excessive expiratory force is exerted, such as by coughing.

The speaking valve could be provided by other one-way valves instead of the flexible flap valve.

The speaking valve 30 is angularly displaceable relative to HME device 22 through 90° from one position or state where the side openings 36 in the speaking valve are aligned with the opposite ends of the main body portion 24 housing the HME elements 28 and 29. In this position air can flow from the tracheostomy tube 10 in and out through the HME elements 28 and 29 so that normal heat and moisture exchange can take place. In this position, the major part of exhalation through the speaking valve 30 is blocked by the action of the flap valve. Also, because the resistance to flow during inhalation is less via the HME elements than via the speaking valve 30, there is no substantial inhalation flow via the speaking valve so that inhalation air flows preferentially through the HME elements 28 and 29. When the speaking valve 30 is rotated through 90° the side openings 36 in the valve move out of alignment with the ends of the body portion 24 and move into a position where they are both blocked by contact with the inner surface of the wall of the cavity 26 in the housing 23. It can be seen that, in this position, flow from the tracheostomy tube 10 to and from the HME elements 28 and 29 is blocked so that air flows preferentially through the speaking valve 30. As the speaking valve 30 only opens to allow inhalation, all expiratory flow is diverted through the fenestrations 15 in the tube 10, up to the vocal folds to enable speech.

There are other arrangements in which apparatus including both an HME element and a speaking valve could be arranged such that in one state flow through the HME element is enabled preferentially to flow through the speaking valve and in the other state flow through the speaking valve is preferentially through the HME element. These other arrangements do not necessarily require the speaking valve to be rotated or otherwise displaced.

Figure 4:
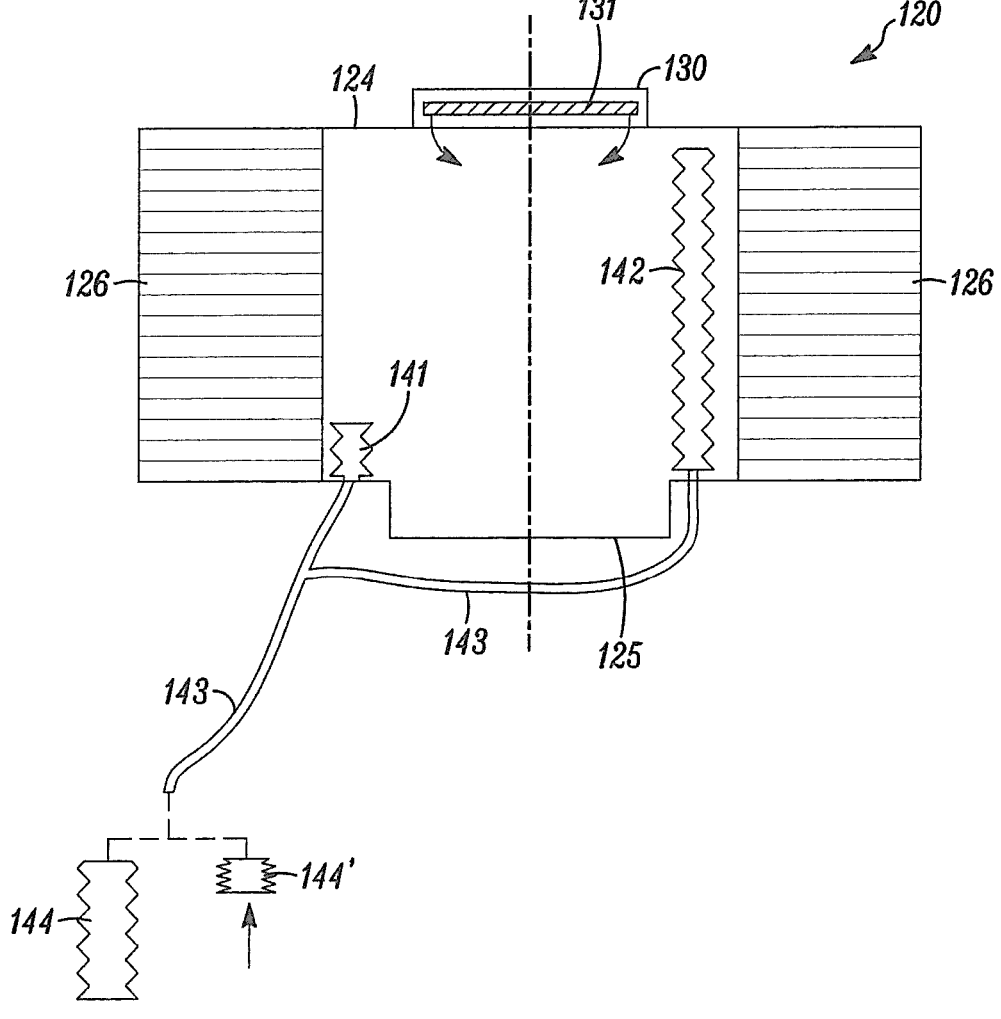
FIG. 4 is a plan, sectional view of an alternative form of combined speaking valve and HME apparatus with opposite ends in different states.

FIG. 4 shows such an apparatus 120 and is divided into two along the axis of the tracheostomy connector 125 with the left-hand side illustrating a state where the HME elements 126 are substantially uncovered so that air flows through the HME elements in preference to flowing through the speaking valve 130. The right-hand side illustrates a state where the HME element 126 is covered or blocked so that air flows through the speaking valve 130 during inhalation. More particularly, the apparatus has a main body portion 124 of tubular shape with an HME element 126 mounted in opposite ends. Although the HME elements 126 and the main body portion could be of circular shape it would be preferable for them to be square or rectangular. Midway along its length the short tracheostomy tube coupling 125 projects outwardly. On the opposite side of the main body portion 124, diametrically opposite the tracheostomy coupling 125, the speaking valve 130 is fixed with a flexible flap 131 that flexes inwardly to allow inhalation but is urged outwardly to seal and prevent (or substantially restrict) flow when the patient exhales. The speaking valve 130 may be a separate component removably attached with the main body 124 or it may be a permanent part of it. Inside the main body portion 124 there is occlusion means in the form of two shutters 141 and 142 positioned close to and inwardly of the respective HME elements 126. The shutters may be of various different kinds and could be operated electrically or mechanically but in the present example they take the form of two inflatable bellows 141 and 142 connected via small bore tubing 143 to a common, small, manually-compressible actuator in the form of a bulb or bellows shown in its natural uncompressed state as 144 and in its compressed or actuated state as 144'. The shutter bellows 141 and 142 have a natural compressed state, as shown in the left-hand side of FIG. 4, in which both HME elements 126 are uncovered so that air can flow in or out of the apparatus through the elements as the patient inhales and exhales. The square or rectangular shape of the HME elements 126 makes it easier for them to be covered by such shutters. When the patient inhales through the HME elements 126 the speaking valve 130 is arranged such that the pressure drop in the apparatus is insufficient to open the speaking valve and allow any significant flow in through the valve. When the patient wishes to speak, he squeezes the bulb to the compressed state 144', thereby inflating and expanding both bellows 141 and 142 substantially to block flow through the HME elements 126.

The apparatus need not have two HME elements but could just have one element.

The invention claimed is:

1. Medico-surgical apparatus adapted for fitting with a machine end of a tracheostomy tube, characterised in that the apparatus includes a housing having both a one-way speaking valve and at least one HME element, that the apparatus is arranged such that in one state flow through the at least one HME element is enabled preferentially to flow through the speaking valve and in another state inhalation flow through the speaking valve is enabled preferentially to flow through the at least one HME element, that the speaking valve has a portion arranged to block a passage through the HME element in the other state, that the portion of the speaking valve is a cylindrical sleeve angularly displaceable within the housing, and that the sleeve has an opening that aligns with the at least one HME element in the one state.

2. The medico-surgical apparatus according to claim 1, characterised in that the speaking valve is fitted with the housing in a manner that enables the speaking valve to be displaced out of the housing by an excessive expiratory force.

3. The medico-surgical apparatus according to claim 1, characterised in that the apparatus has a coupling adapted for fitting with the machine end of the tracheostomy tube, a body portion extending transversely of the coupling, the at least one HME element and an other HME element at opposite ends of the body portion and a cavity aligned with the coupling in which the speaking valve is angularly displaceably received for displacement between the one and other states.

4. The medico-surgical apparatus according to claim 1, characterised in that the apparatus includes occlusion means operable separately of the speaking valve to prevent or enable flow through the or each HME element.

5. The medico-surgical apparatus according to claim 4, characterised in that the occlusion means is pneumatically operable, and that the apparatus includes a pneumatic actuator.

6. The medico-surgical apparatus according to claim 4, characterised in that the occlusion means includes a bellows expansible to block flow through the or each HME element.

7. The medico-surgical apparatus according to claim 5, characterised in that the occlusion means includes a bellows expansible to block flow through the or each HME element.

8. An assembly of a tracheostomy tube and medico-surgical apparatus according to claim 1, wherein the medico-surgical apparatus is fitted with the machine end of the tracheostomy tube.

* * * * *